US007202362B2

(12) United States Patent
Thummel et al.

(10) Patent No.: US 7,202,362 B2
(45) Date of Patent: Apr. 10, 2007

(54) TRANSITION METAL COMPLEXES FROM SOLID STATE SYNTHESIS

(75) Inventors: Randolph P. Thummel, Houston, TX (US); Yi-Zhen Hu, Houston, TX (US)

(73) Assignee: University of Houston, Houston, TX (US)

( * ) Notice: Subject to any disclaimer, the term of this patent is extended or adjusted under 35 U.S.C. 154(b) by 200 days.

(21) Appl. No.: 10/795,838

(22) Filed: Mar. 8, 2004

(65) Prior Publication Data

US 2004/0225122 A1    Nov. 11, 2004

Related U.S. Application Data

(60) Provisional application No. 60/453,068, filed on Mar. 7, 2003.

(51) Int. Cl.
C07D 401/14    (2006.01)
C07D 471/02    (2006.01)

(52) U.S. Cl. ............... 546/5; 546/10; 546/81; 546/152; 502/104

(58) Field of Classification Search ............ 546/5, 546/10, 81, 152; 502/104
See application file for complete search history.

(56) References Cited

OTHER PUBLICATIONS

Alonso-Vante, N.; Jean-Francois, N.; Sauvage, J.-P. "Spectral Sensitization of Large-band-gap semiconductors (Thin Films and Ceramics) by a Carboxylated Bis(1-10-Phenathroline)copper(I) Complex," *J. Chem. Soc., Dalton Trans.* 1994, pp. 1649-1654.
Argazzi, R.; Bignozzi, C. A.; Heimer, T. A.; Castellano, F. N.; Meyer, G. "Enhanced Spectral Sensitivity from Ruthenium(II) Polypyridyl Based Photovoltaic Devices," *J.Inorg. Chem.* 1994, vol. 33, pp. 5741-5759.
Armaroli, N. "Photoactive mono- and polynuclear Cu(I)-phenanthrolines. A viable alternative to Ru(II)-polypyridines?," *Chem. Soc. Rev.* 2001, vol. 30, pp. 113-124.
Beley, M.; Bignozzi, C.-A.; Kirsch, G.; Alebbi, M.; Raboin, J.-C. "New ruthenium bisterpyridinyl complexes, as efficient sensitizers of nanocrystalline, TiO₂ films," *Inorganica Chimica Acta* 2000, vol. 318, pp. 197-200.
Bignozzi, C. A.; Argazzi, R.; Kleverlaan, C. J. "Molecular and supramolecular sensitization of nanocrystalline wide band-gap semiconductors with mononuclear and polynuclear metal complexes," *Chem. Soc. Rev.* 2000, vol. 29, pp. 87-96.
Hagfeldt, A.; Grätzel, M. "Molecular Photovoltaics," *Acc. Chem. Res.* 2000, vol. 33, pp. 269-277.
Hara, K.; Sugihara, H.; Singh, L. P.; Islam, A.; Katoh, R.; Yanagida, M.; Sayama, K.; Murata, S.; Arakawa, H. "New Ru(II) phenanthroline complex photosensitizers having different number of carboxyl groups for dye-sensitized solar cells," *Journal of Photochemistry and Photobiology A: Chemistry* 2001, vol. 145, pp. 117-122.
Hara, K.; Sugihara, H.; Tachibana, Y.; Islam, A.; Yanagida, M.; Sayama, K.; Arakawa, H. "Dye-Sensitized Nanocrystalline TiO₂ Solar Cells Based on Ruthenium(II) Phenanthroline Complex Photosensitizers," *Langmuir* 2001, vol. 17, pp. 5992-5999.
Hara, K.; Horiuchi, H.; Katoh, R.; Singh, L. P.; Sugihara, H.; Sayama, K.; Murata, S.; Tachiya, M.; Arakawa, H. "Effect of the Ligand Structure on the Efficiency of Electron Injection from Exited Ru-Phenanthroline Complexes to Nanocrystalline TiO₂ Films," *J. Phys. Chem. B* 2002, vol. 106, pp. 374-379.
Islam, A.; Sugihara, H.; Singh, L. P.; Hara, K.; Katoh, R.; Nagawa, Y.; Yanagida, M.; Takahashi, Y.; Murata, S.; Arakawa, H. "Synthesis and photophysical properties of ruthenium(II) charge transfer sensitizers containing 4,4'-dicarboxy-2,2'-biquinoline and 5,8-dicarboxy-6,7-dihydro-dibenzo[1,10]-phenanthroline," *Inorganica Chimica Acta* 2001, vol. 322, pp. 7-16.
Kalyanasundaram, K.; Grätzel, M. "Applications of functionalized transition metal complexes in photonic and optoelectronic devices," *Coordination Chemistry Reviews* 1998, vol. 77, pp. 347-414.
Kelly, C. A.; Meyer, G. J. "Excited state processes at sensitized nanocrystalline thin film semiconductor interfaces," *Coordination Chemistry Reviews* 2001, vol. 211, pp. 295-315.
Nazeeruddin, M. K.; Kay, A.; Rodicio, I.; Humphry-Baker, R.; Müller, E.; Liska, P.; Vlachopoulos, N.; Grätzel, M. "Conversion of Light to Electricity by cis-$X_2$Bis(2,2'-bipyridyl-4-4'-dicarboxylate)ruthenium(II) Charge-Transfer Sensitizers (X=Cl⁻, Br⁻,I⁻, CN⁻, and SCN) on Nanocrystalline TiO₂ Electrodes," *J. Am. Chem. Soc.* 1993, vol. 115, pp. 6382-6390.
Nazeeruddin, M. K.; Péchy, P.; Renouard, T.; Zakeeruddin, S. M.; Humphry-Baker, R.; Comte, P.; Liska, P.; Cevey, L.; Costa, E.; Shklover, V.; Leone, S.; Deacon, G. B.; Bignozzi, C. A.; Grätzel, M. "Engineering of Efficient Panchromatic Sensitizers for Nanocrystalline TiO₂-Based Solar Cells," *J. Am. Chem. Soc.* 2001, vol. 123, pp. 1613-1624.
Sakaki, S.; Kuroki, T.; Hamada, T. "Synthesis of a new copper(I) complex, Cu(tmdcbpy=4,4',6,6'-tetramethyl-2,2'-bipyridine-5,5'-dicarboxylic acid), and its application to solar cells," *J. Chem. Soc., Dalton Trans.* 2002, pp. 840-842.
Schwarz, O.; van Loyen, D.; Jockusch, S.; Turro, N. J.; Dürr, H. "Preparation and application of new ruthenium(II) polypyridyl complexes as sensitizers for nanocrystalline TiO₂," *Journal of Photochemistry and Photobiology A: Chemistry* 2000, vol. 132, pp. 91-98.
Yanagida, M.; Islam, A.; Tachibana, Y.; Fujihashi, G.; Katoh, R.; Sugihara, H.; Arakawa, H. "Dye-sensitized solar cells based on nanocrystalline TiO₂ sensitized with a novel pyridylquinoline ruthenium(II) complex," *New J. Chem.* 2002, vol. 26, pp. 963-965.
Zakeeruddin, S. M.; Nazeeruddin, M. K.; Humphry-Baker, R.; Grätzel, M. "Stepwise Assembly of Tris-Heteroleptic Polypyridyl Complexes of Ruthenium(II)," *Inorg. Chem.* 1998, vol. 37, pp. 5251-5259.

*Primary Examiner*—Charanjit S. Aulakh
(74) *Attorney, Agent, or Firm*—Jackson Walker L.L.P.

(57) ABSTRACT

Methods and compositions related to the synthesis of photosensitizers of titanium dioxide performed in situ, stepwise, in the solid state, and directly on the surface of the titanium dioxide semiconductor material. The method is generally accomplished by first absorbing an anchor ligand onto the titanium dioxide semiconductor material, then adding an appropriate transition metal, and finally adding one or more secondary ligands to complete the synthesis of the transition metal complex or sensitizer.

16 Claims, 6 Drawing Sheets

Figure 5

| TiO₂-Anchor Ligand | Metal salt | Intermediate | UV | Second Ligand | Heteroleptic Complex | UV |
|---|---|---|---|---|---|---|
| | [Cu(CH₃CN)₄]⁺ | | yes | biq | | yes |
| | [Cu(CH₃CN)₄]⁺ | | yes | mph | | yes |
| | [Cu(CH₃CN)₄]⁺ | | yes | mbp | | yes |
| | [Cu(CH₃CN)₄]⁺ | | yes | bap | | yes |

TRANSITION METAL COMPLEXES FROM SOLID STATE SYNTHESIS

BACKGROUND

This application claims priority to U.S. Provisional Patent Application Ser. No. 60/453,068, filed Mar. 7, 2003, the entire content of which is hereby incorporated by reference.

This invention generally relates to photosensitizers for titanium dioxide having transition metal complexes on the surface of the titanium dioxide and their solid state methods of synthesis.

The use of sensitized semi-conductors for the direct conversion of sunlight into electricity is an attractive alternative to more traditional fossil fuel based energy production. A photovoltaic cell called the Grätzel cell, after inventor Michael Grätzel, has become the industry standard to date. This cell uses a Ru(II) due, involving the anchor ligand 4,4'-dicarboxy-2,2'-bipyridine, to sensitize titanium dioxide ($TiO_2$). With an efficiency of only about 10% and a fairly high cost due to the transition metal catalyst Ru(II), the dye-sensitizer solar cell has not yet found widespread commercial utility.

The principle set-up and operation of the dye-sensitized solar cell begins with light absorption (such as light energy from the sun) by a dye chemically absorbed on a semiconductor coated on the surface of a glass electrode. The semiconductor film is in contact with an iodide/triiodide redox electrolyte. A glass counter electrode plate is situated over the semiconductor and the edges of the two glass plates are sealed. After the absorption of a photon of light, the dye, typically a transition metal complex whose molecular properties are specifically engineered for the task, is able to transfer an electron to the semiconductor. The electric potential developed inside the bulk material causes the flow of electrons through the semiconductor film to a conducting glass electrode. After passing through an external circuit and having delivered power to a load, the electrons return to the cell at the counter electrode. Triiodide is then converted to iodide which reduces the photo-oxidized dye to its original ground state. Ru(II) is the metal chromophore present in the dye-sensitized solar cells used today.

Current solar cell technology involves the absorption or doping of transition metal complexes as sensitizers onto a nanocrystalline semiconductor such as titanium dioxide ($TiO_2$). Titanium dioxide is a semiconductor that is useful in the conversion of visible and ultraviolet radiation into electricity. Such conversion depends upon the injection of photoexcited electrons into the conduction band of the titanium dioxide. This photoinjection is accomplished by a sensitizer or dye, which absorbs incident radiation, thereby becoming a high energy, photoexcited material. This photoexcited material can then inject an electron, or sensitize, the titanium dioxide, thereby rendering it as conducting and creating an electric current.

A critical component of such a photosensitized device is the sensitizer or dye, because it determines the efficiency of electron injection into the titanium dioxide and thus the efficiency of the device (Nazeeruddin et al., 1993; Bignozzi et al., 2000; Schwarz et al., 2000). Sensitizers or dyes are typically deeply colored materials that absorb light in the visible and ultraviolet region of the spectrum. They are traditionally prepared independent of the titanium dioxide by a series of synthetic steps involving both organic and inorganic chemical methodology (Nazeeruddin et al., 2001). These preparations involve the actual synthesis, followed by purification or isolation of the product, followed by identification or characterization of this product. Purification and characterization may occur at each and every step of the traditional synthetic method. The prepared sensitizer is then applied to the surface of the titanium dioxide to provide the sensitized semiconductor. The efficiency of charge injection is measured by a variety of techniques. Numerous sensitizers have been prepared and tested according to this protocol (Hagfeldt et al., 2000; Kalyanasundaram et al., 1998; Kelly et al., 2001).

The vast majority of previously prepared sensitizers have been complexes of Ru(II) (Beley et al., 2000; Hara et al., *J. Photochemistry and Photobiology* 2001, *Langmuir* 2001, and *J. Phys. Chem. B* 2002; Islam et al., 2001; and Yanagida et al., 2002). The limiting factor in the testing of many different sensitizers is the synthesis of the sensitizer.

What is needed, therefore, is a faster and more efficient method for synthesizing transition metal complexes which may serve as sensitizers for titanium dioxide.

SUMMARY

One embodiment of the current invention relates to photosensitizers for titanium dioxide and a method for carrying out the solid state synthesis of transition metal complexes which are sensitizers for titanium dioxide. In particular, one embodiment of the current invention relates to a new in situ solid state method for synthesizing photosensitizers of titanium dioxide.

The present invention provides a general method for the stepwise synthesis of transition metal complexes directly on the surface of the titanium dioxide semiconductor material. The method is a much simpler and more efficient synthetic technique. In particular, by preparing the sensitizer directly on the surface of the titanium dioxide, the lengthy and tedious independent preparation and final absorption of the sensitizer onto the titanium dioxide is avoided. Furthermore, the amounts of material required for the in situ solid state synthesis are extremely small. The in situ solid state synthesis method also does not require purification at any stage. Unwanted side products or reagents not anchored to the titanium dioxide are merely washed away with solvent after each preparative step (Zakeeruddin et al., 1998).

The in situ solid state synthesis method also allows for the preparation of transition metal complexes which would be difficult or impossible to prepare using conventional solution techniques. As an example, asymmetrical complexes involving Cu(I), such as CuLL', cannot be made in solution due to exchange of the ligands L and L'. These asymmetrical complexes may be synthesized in the solid state, where exchange does not occur readily, thereby enabling the preparation of heteroleptic complexes (Alonso-Vante et al., 1994; Armaroli, 2001; Sakaki et al., 2002).

The simplification of the synthesis and doping procedures allows for the creation and examination of a wide variety of untested metals and ligands. Variation of metals and ligands provides a combinatorial-type approach to the investigation of semiconductor sensitization.

The general steps for the in situ solid state synthesis method are shown schematically in FIG. 1. The method is essentially combinatorial in its approach, allowing the facile preparation of a wide variety of transition metal complexes as sensitizers for titanium dioxide by using different anchor ligands, metal ions, and secondary ligands. First, an anchor ligand is absorbed onto the titanium dioxide. Second, a transition metal cation is incorporated into the photosensitizer structure. The last step involves the incorporation of secondary ligands into the structure. More than one secondary ligand may be utilized in each complex.

Another embodiment of the present invention is a photosensitizer having the following general structure:

TiO$_2$-Anchor Ligand-M-Secondary Ligand

In this structure, the anchor ligand has an anchoring end which is attached to the titanium dioxide and a chelating end which is associated with the metal cation. M is a metal cation, such as a transition metal cation. M may have a number of ligands or counteranions attached to it both before and after it becomes incorporated into the photosensitizer, depending on the valency of M. The number of ligands initially attached to the metal cation may be reduced by the number of associations the metal cation has with the neighboring nitrogen atoms. The secondary ligand may be one or more secondary ligands. The photosensitizer structure is a heteroleptic complex, having a transition metal ion in association with more than one ligand.

The terms sensitizer, sensitizer complex, photosensitizer, photosensitizer complex, dye, and transition metal complex are used interchangeably to refer to the photosensitizer of the current invention.

Characterization of the photosensitizer complex is based primarily on absorption and redox properties, which are the two measurable characteristics having a strong relevance to the efficiency of charge injection into the titanium dioxide.

BRIEF DESCRIPTION OF THE DRAWINGS

FIG. 5 shows a chart with several representative photosensitizers, their components, their intermediate structures, and UV absorption test confirmations.

DETAILED DESCRIPTION OF PREFERRED EMBODIMENTS

One embodiment of the present invention is a method for the stepwise, in situ, solid state synthesis of photosensitizers of titanium dioxide.

Figure 1:
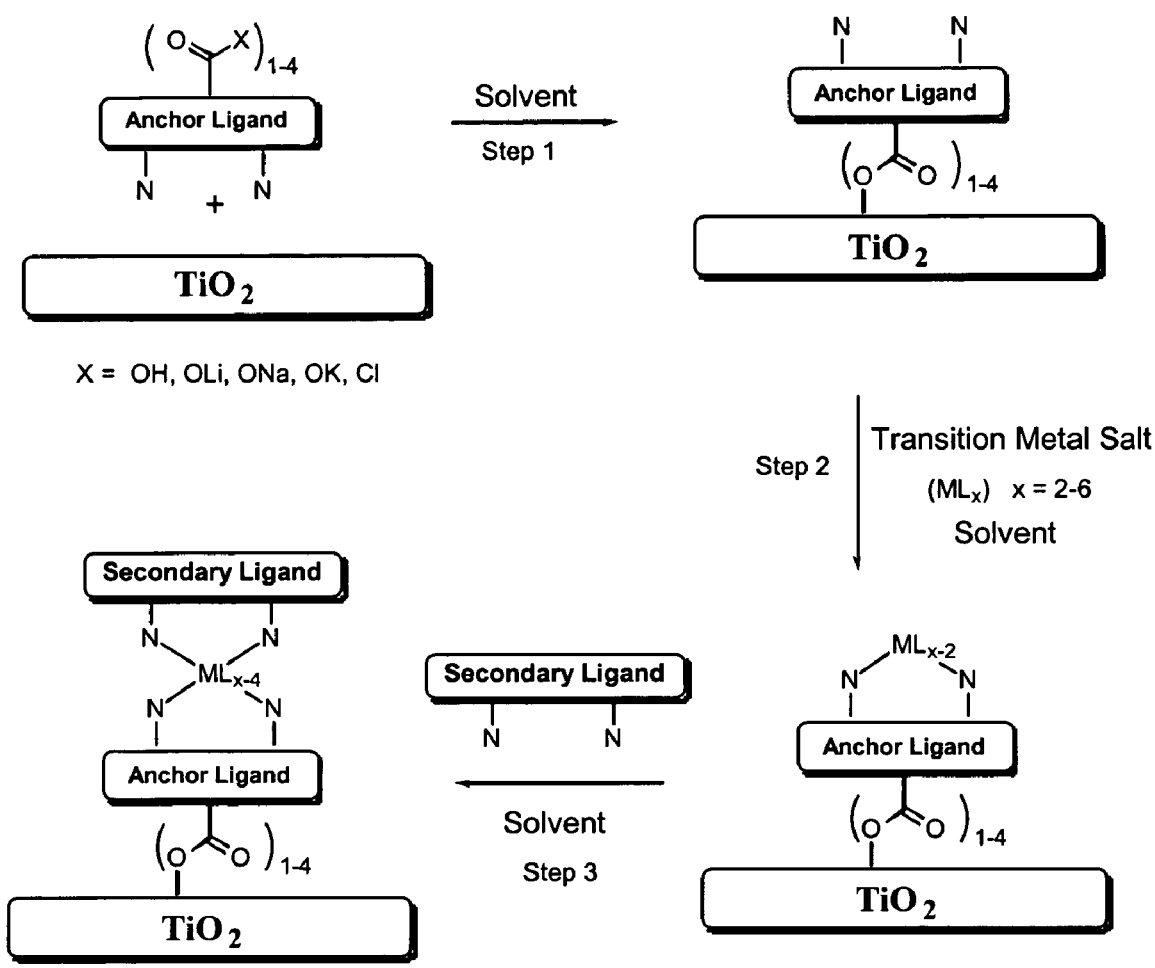
FIG. 1 shows a schematic representation of a general process for synthesizing the photosensitizer complex.

A general process for fabricating the photosensitizer on the surface of titanium dioxide is shown in a schematic form in FIG. 1. The method is generally accomplished by first absorbing an anchor ligand onto the titanium dioxide semiconductor material, then adding an appropriate transition metal, and finally adding one or more secondary ligands to complete the synthesis of the transition metal complex or sensitizer.

Figure 2:
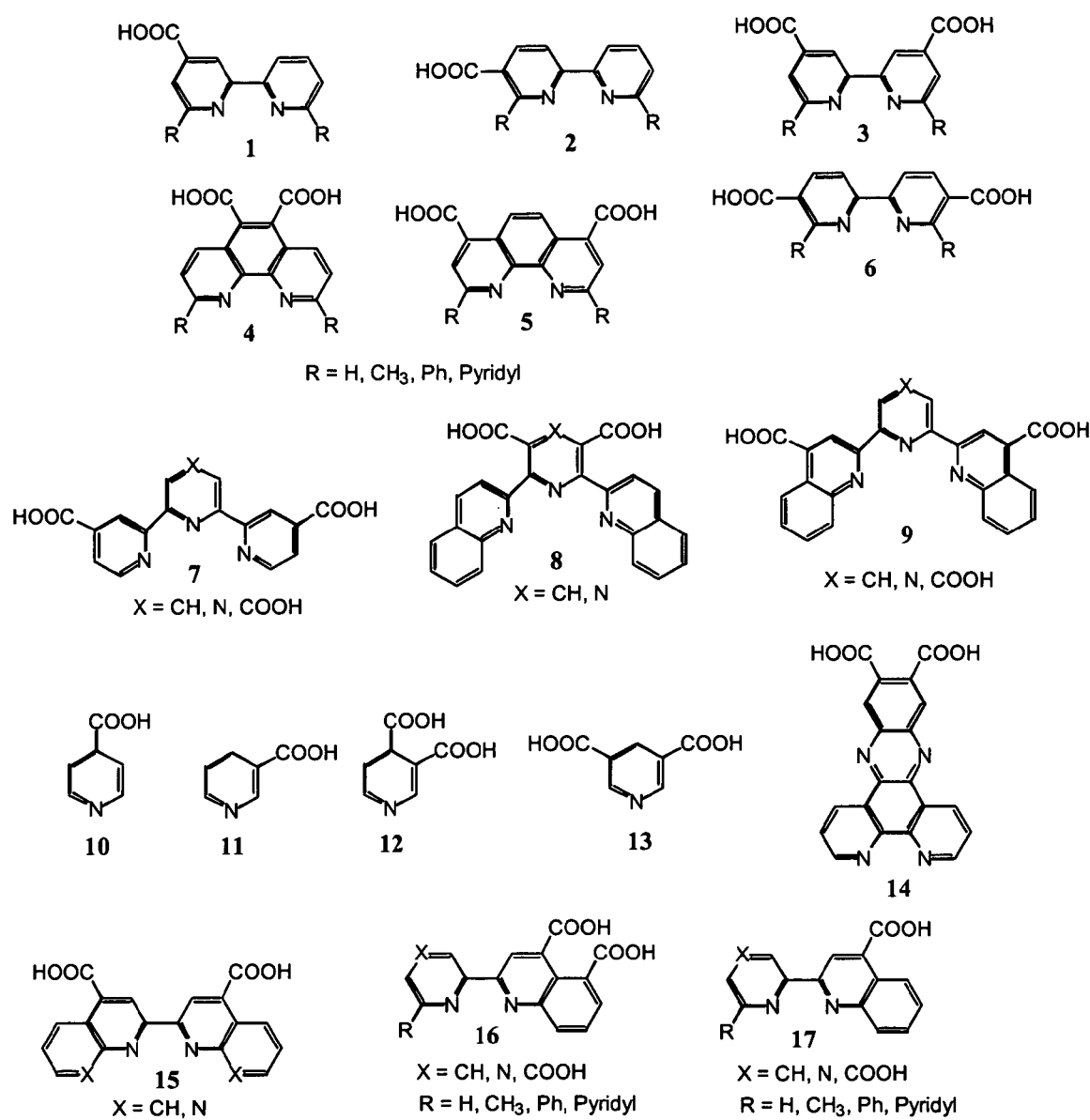
FIG. 2 shows representative examples of the anchor ligands.

The initial step in the process involves absorption of the anchor ligand onto the titanium dioxide semiconductor material. The anchor ligand can have one to four azaaromatic rings covalently joined to each other with between one and three covalent bonds. The anchor ligand has an anchoring end, for attachment to the titanium dioxide, and a chelating end, for association with the metal cation. The anchoring end of the anchor ligand may have any of several groups capable of binding with the titanium dioxide, including, for example, carboxy groups. The chelating end of the anchor ligand may have any of several atoms capable of associating with the metal cation, including, for example, nitrogen atoms. The perimeter of the azaaromatic ring system can be substituted with one to four carboxy groups either as the free carboxylic acid or its Group I salt. Examples of Group I salts include lithium, sodium, and potassium salts. The corresponding carboxylic acid chloride can also be used. The carboxy groups can be attached in place of any hydrogen on the perimeter of the anchor ligand, but there can be only one carboxy group at any given ring position. A listing of representative anchor ligands is shown in FIG. 2.

The anchor ligand should be dissolved in a solvent at a reasonable concentration. A preferred concentration of the anchor ligand is between about $10^{-2}$ M and about $10^{-5}$ M. Examples of preferred solvents for the anchor ligand are water, methanol, ethanol, isopropanol, 1-butanol, ethylene glycol, acetonitrile, acetone, chloroform, dichloromethane, ethylacetate, dioxane, nitromethane, N,N-dimethylformamide ("DMF"), dimethylsulfoxide ("DMSO"), N,N-dimethylacetamide, HMPA, and acetic acid.

To carry out an embodiment of the synthetic method, a glass plate coated with titanium dioxide is first prepared in the normal fashion (Argazzi et al., 1994). The coated glass plate is then dipped into a solution of the anchor ligand in its appropriate solvent for a period of from about one to about 24 hours. The solvent should preferably be at a temperature of about 20° C. to about 150° C. The plate is then removed, rinsed with the solvent, and air dried. The degree of loading of the anchor ligand can be determined by desorbing the ligand into $10^{-2}$ M KOH, measuring the absorbance of this solution and comparing it to a similar solution of known concentration.

The second step of the process involves incorporation of the transition metal cation. The transition metal cation is incorporated by means of its salt. Any transition metal salt can be used. The transition metal salt can contain only inorganic ligands and counterions, or it can contain an organic ligand in addition to any appropriate inorganic ligands and ions required to complete the coordination sphere and balance the charge. The transition metal cation preferably has a total of between two and six ligands and counterions attached to it, depending on the valency of the cation. The transition metal salt should also be dissolved in a solvent at a reasonable concentration. A preferred concentration of the transition metal salt is between about $10^{-2}$ M and about $10^{-5}$ M. Examples of preferred solvents include those listed above, which can also be used with the anchor ligand.

To incorporate the transition metal cation, the glass plate previously loaded with anchor ligand and dried is dipped into a solution of the transition metal salt in its appropriate solvent for a period of from about one to about 24 hours. The solvent should preferably be at a temperature of about 20° C. to about 150° C. The plate is then removed, rinsed with the solvent, and air dried. Generally, a color change will indicate absorption of the metal cation.

Figure 3:
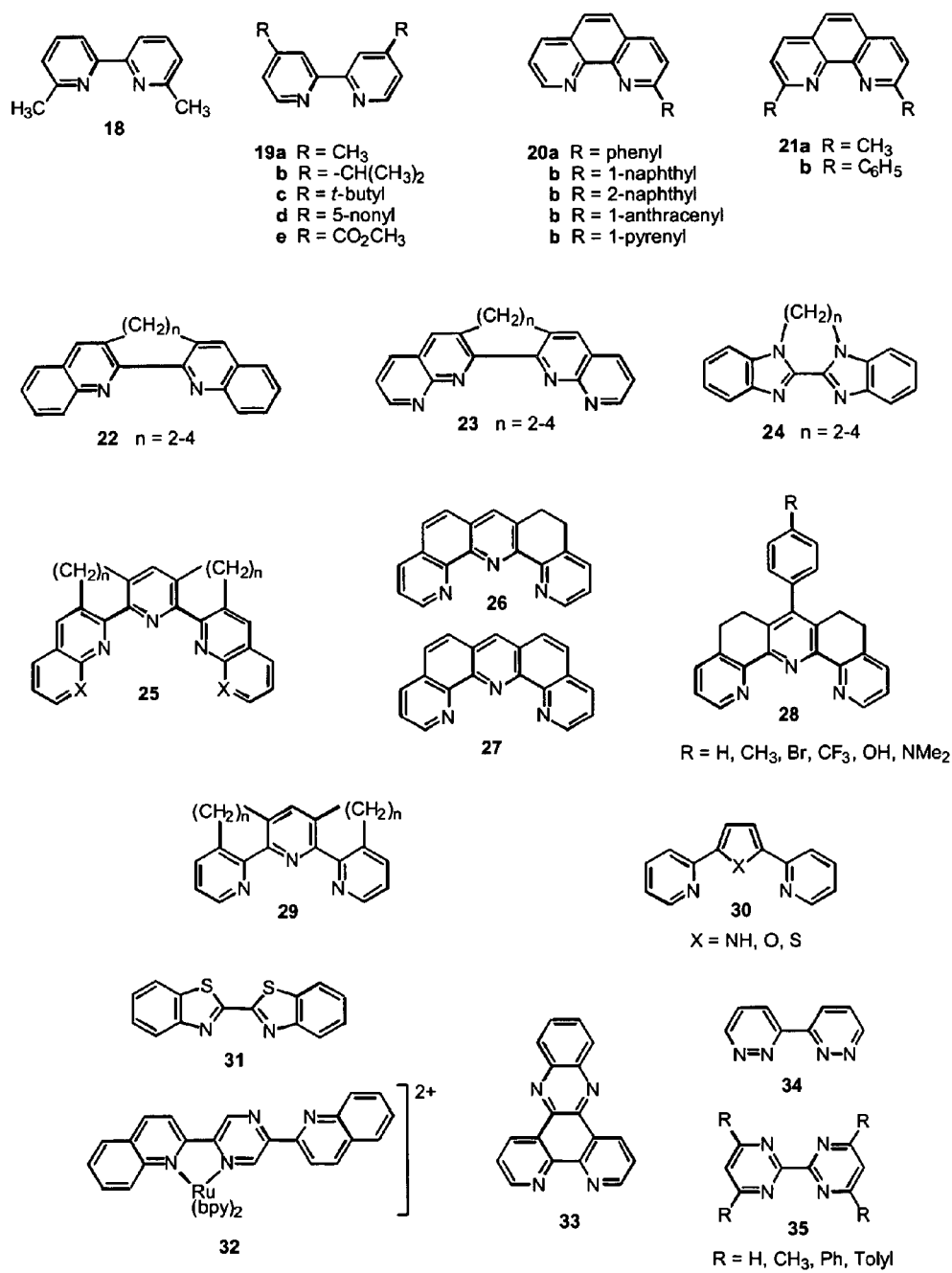
FIG. 3 shows representative examples of the secondary ligands.

In the final steps, one or more secondary ligands are incorporated into the photosensitizer structure. The secondary ligand can be any ligand which is capable of binding to the transition metal cation to help complete the coordination sphere of the metal. A wide variety of organic and inorganic ligands can be used. Examples of these secondary ligands are shown in FIG. 3. If more than one secondary ligand is to be incorporated, this incorporation could be done in a stepwise fashion, with only one secondary ligand incorporated in one step. Or, the secondary ligand could already have been attached to the metal atom and could be incorporated in the same step with the metal atom. The secondary ligand to be incorporated should be dissolved in a solvent at a reasonable concentration. A preferred concentration of the secondary ligand is between about $10^{-2}$ M and about $10^{-5}$ M. Examples of preferred solvents include those listed above, which can also be used with the anchor ligand and the transition metal salt.

In additional embodiments, the metal cation and the one or more secondary ligands are incorporated into the photosensitizer structure in one step, utilizing one metal cation/secondary ligand compound.

To incorporate the desired secondary ligand, the dried glass plate previously loaded with anchor ligand and transition metal cation is dipped into a solution of the secondary ligand in its appropriate solvent for a period of from about one to about 24 hours. The solvent should preferably be at a temperature of about 20° C. to about 150° C. The plate is then removed, rinsed with the solvent, and air dried. Generally, a color change will indicate absorption of the secondary ligand. If more than one ligand is required to complete the coordination sphere of the metal, a second or even third dipping may be appropriate.

An additional preferred embodiment of the present invention is a photosensitizer prepared in accordance with the method described above.

A further preferred embodiment of the present invention pertains to a photosensitizer having the following general structure:

TiO$_2$-Anchor Ligand-M-Secondary Ligand

In this structure, TiO$_2$ is the titanium dioxide semiconductor material. M is a metal cation, such as a transition metal cation.

The anchor ligand has an anchoring end and a chelating end. The anchoring end can be a carboxy group, while the chelating end can be one or nitrogen atoms. The anchor ligand can be any structure having one to four azaaromatic rings covalently joined to each other with between one and three covalent bonds. The perimeter of the azaaromatic ring system can be substituted with one to four carboxy groups, which serve as the anchoring end of the anchor ligand. The carboxy groups on the anchor ligand can be at any position of the azaaromatic rings, attached in place of any hydrogen, but there can be only one carboxy group at any given ring position. At least one carboxy group is covalently linked to the titanium dioxide semiconductor material through an ester linkage, which tethers the anchoring end of the anchor ligand to the titanium dioxide semiconductor material. Between one and four carboxy groups can be covalently attached via ester linkages to the titanium dioxide. Examples of representative anchor ligands are shown in FIG. 2.

The metal cation ("M") can be any transition metal cation. Particular examples of the metal cation include Ru, Cr, Mn, Fe, Co, Ni, Cu, Zn, Rh, Pd, Ag, In, Re, Os, Ir, and Pt. The metal cation preferably contains between two and six ligands or counterions. The metal cation can contain inorganic ligands, organic ligands, counterions, or any combination thereof required to complete the coordination sphere and balance the charge. The number of ligands originally present on the transition metal cation may be decreased by the number of associations the metal cation forms with the nitrogen atoms in the anchor ligand and the secondary ligand. The metal cation is incorporated into the photosensitizer structure through association with the chelating end of the anchor ligand, or preferably through association with the nitrogen atoms present in the azaaromatic rings of the anchor ligand.

The secondary ligand can be any ligand which is capable of binding to the transition metal cation to help complete the coordination sphere of the metal. A wide variety of organic and inorganic ligands can be used. Preferred examples of the secondary ligand have one or more heterocyclic rings containing nitrogen atoms. The heterocyclic rings may be further substituted with a variety of substituents. Particular examples of the secondary ligands are shown in FIG. 3. In some embodiments, the secondary ligand in the above structure represents more than one secondary ligand. The one or more secondary ligands are incorporated into the photosensitizer structure through complexation between the nitrogen atoms of the secondary ligands and the metal cation. In some embodiments, the metal cation and the one or more secondary ligands are incorporated into the photosensitizer structure in one step, utilizing one metal salt/secondary ligand structure.

EXAMPLE 1

Freshly prepared titanium dioxide (TiO$_2$) was coated onto a glass plate in the normal fashion (Argazzi et al., 1994). The plate was then dipped into a $3\times10^{-4}$ M solution of 4,4'-dicarboxy-2,2'-biquinoline in ethanol for a period of 24 hours, washed thoroughly with ethanol, then air dried at room temperature. The presence of the anchored ligand was verified by IR comparison of TiO$_2$ containing the adsorbed ligand with the pure ligand. The adsorption was quantified by desorbing the ligand into 0.1 M KOH (1:1 EtOH/H$_2$O) and measuring the UV band at 260 nm. The loading was measured at $6.3\times10^{-8}$ mol/cm$^2$, which compared reasonably well with traditional dye-sensitized TiO$_2$.

The sensitizer complex was then synthesized in a stepwise fashion from the anchored dicarboxylate ligand. First, the plate was dipped in a $10^{-3}$ M acetonitrile solution of [Cu(CH$_3$CN)$_4$](PF$_6$) for three hours, washed with acetonitrile and air-dried. The plate was then dipped into a $10^{-3}$ M dichloromethane solution of one of five bidentate secondary ligands: (1) 1,10-phenanthroline ("phen"); (2) 4,7-diphenyl-1,10-phenanthroline ("bap"); (3) 2,9-dimethyl-2,2'-bipyridine ("mbp"); (4) 2,9-dimethyl-1,10-phenanthroline ("mph"); and (5) 2,2'-biquinoline ("biq"). The structures of these secondary ligands are illustrated in Examples 2–8 below. The plate was then washed with solvent and air-dried.

Formation of the sensitizer complex in the TiO$_2$ matrix was evidenced by a color change of the glass plate. The characteristic long wavelength MLCT (metal-to-ligand charge transfer) absorption was observed spectrophotometrically. Both the intensities and the energies of the absorption bands were consistent with expectations based on the structures of secondary ligands 1–5. The complexes involving 1,10-phenanthroline and 4,7-diphenyl-1,10-phenanthroline exhibited the weakest bands, because these ligands lack ortho substituents which are well known to stabilize Cu(I) systems. The complexes involving 2,9-dimethyl-1,10-phenanthroline and 2,9-dimethyl-2,2'-bipyridine possess stabilizing ortho-methyl substituents and showed very similar, more intense absorptions. Finally, the complex with 2,2'-biquinoline was also stabilized towards oxidation and appeared at the lowest energy due to the increased electronegativity of the ligand.

Evidence demonstrated that the sensitizer was not just being formed on the surface of the TiO$_2$. When a 2-fold thicker coating of the titanium dioxide semiconductor material was applied to the glass plate, the intensity of the sensitizer absorption increased accordingly.

Stability to oxygen is also a function of the secondary ligand structures. The absorbances associated with the structures incorporating secondary ligands 1 and 2 faded within a few hours after exposure to air, but were more stable under an Argon atmosphere. The other complexes, involving ortho-substituted ligands, were stable to air.

EXAMPLE 2

TiO$_2$-bqda-Cu(I)-biq

A glass plate coated with a TiO$_2$ film was dipped into a saturated solution of 4,4'-dicarboxy-2,2'-biquinoline ("bqda") in DMSO/ethanol (v/v 1:20) for a period of 24 hours, washed thoroughly with ethanol, and then air dried at room temperature. The structure for bqda is shown below:

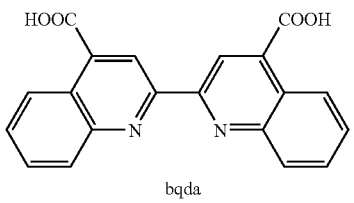

bqda

The copper(I) complex was then synthesized in a stepwise fashion from the anchored dicarboxylate ligand. First, the plate was dipped into a 10$^{-3}$ M acetonitrile solution of [Cu(CH$_3$CN)$_4$](PF$_6$) for 12 hours, rinsed with acetonitrile and air dried. The plate was then dipped into a 10$^{-3}$ M dichloromethane solution of a secondary ligand, 2,2'-biquinoline ("biq") for 3 hours. The structure of the secondary ligand biq is shown below:

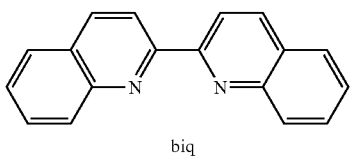

biq

The plate was then washed with dichloromethane and air dried at room temperature.

The structure of the synthesized photosensitizer (Compound 1) is shown below.

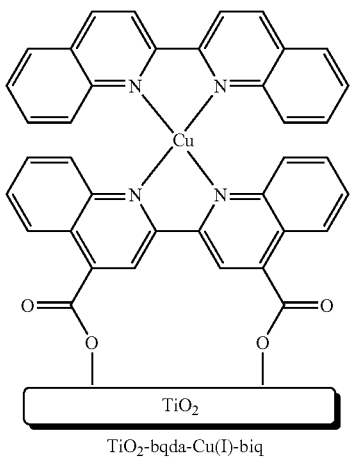

Compound 1

TiO$_2$-bqda-Cu(I)-biq

Figure 4:
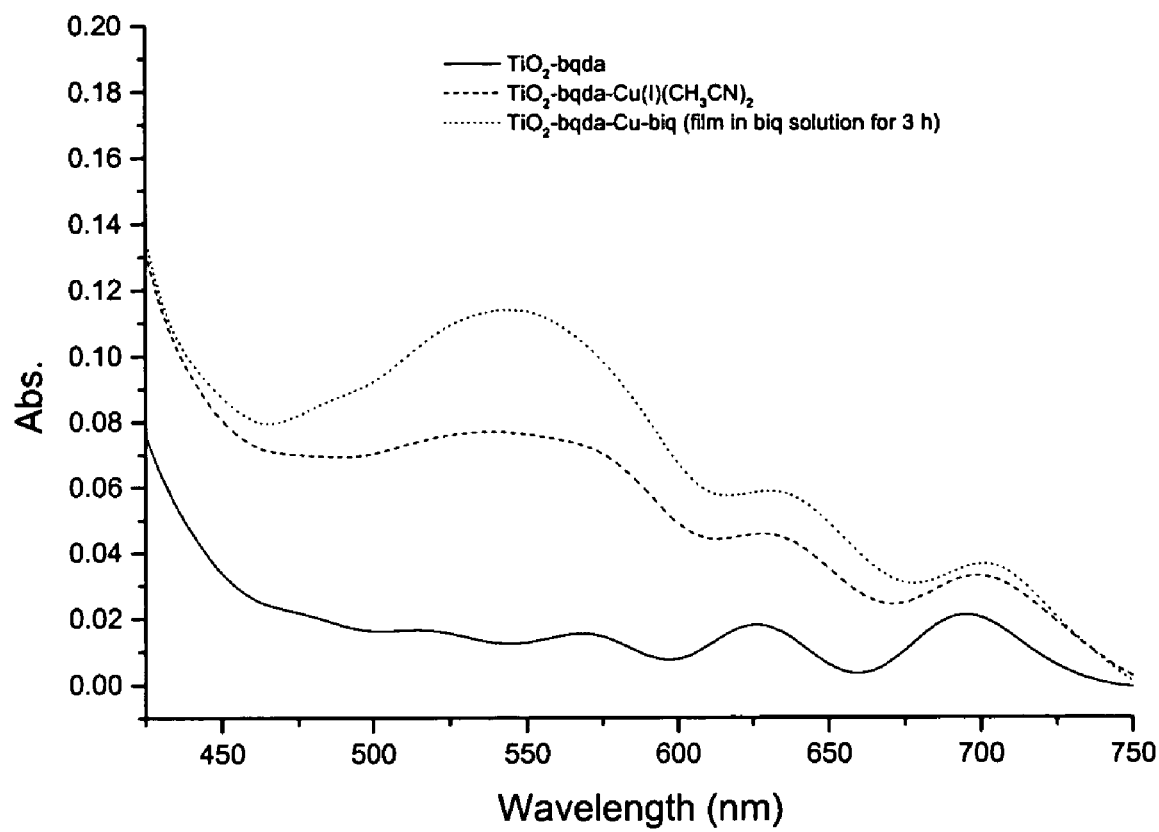
FIG. 4 shows an electronic absorption spectra for an example photosensitizer, illustrating the changes in absorbance at each step of the photosensitizer synthesis.
Figure 6:
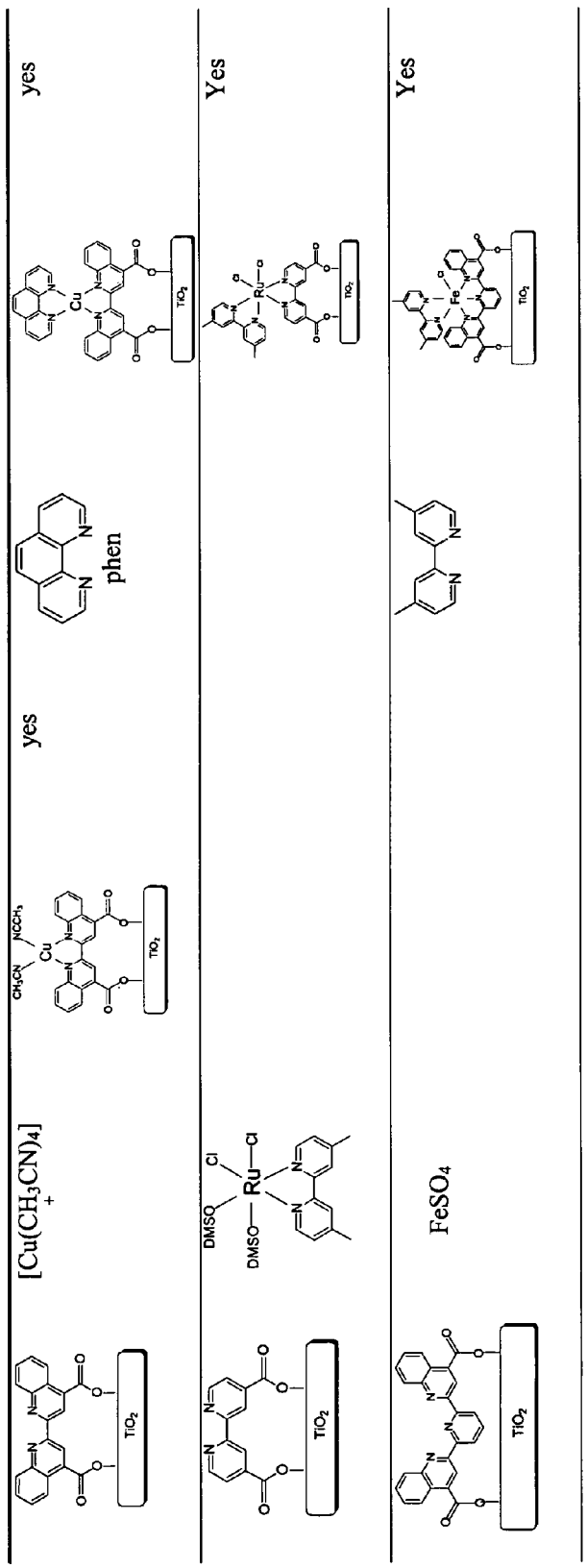
FIG. 6 shows a chart with several additional representative photosensitizers, their components, and, if applicable, their intermediate structures and UV absorption test confirmations.

Formation of the heteroleptic copper (I) complex ([Cu(bqda)(biq)]$^+$) on the TiO$_2$ film was evidenced by a color change (from light red to violet red) of the glass plate and the characteristic long wavelength MLCT (metal-to-ligand charge transfer) absorption at 545 nm, shown in FIG. 4, which was observed spectrophotometrically.

EXAMPLE 3

TiO$_2$-bqda-Cu(I)-mph

The photosensitizer (Compound 2) was prepared according to the procedure described in Example 2, except using 2,9-dimethyl-1,10-phenanthroline ("mph") as the secondary ligand. The structure of mph is shown below:

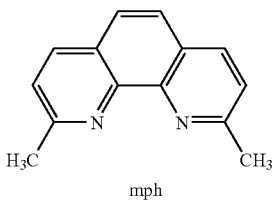

mph

The structure of the synthesized photosensitizer (Compound 2) is shown below.

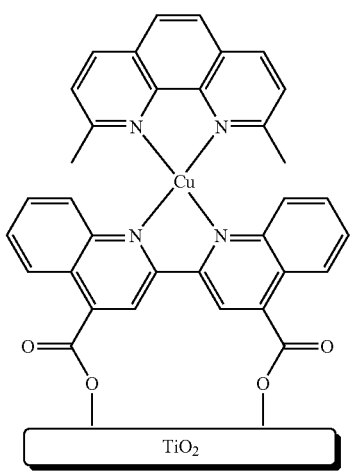

Compound 2

TiO$_2$-bqda-Cu(I)-mph

The characteristic long wavelength MLCT absorption of the heteroleptic copper complex bqda-Cu(I)-mph appeared at 524 nm.

EXAMPLE 4

TiO$_2$-bqda-Cu(I)-mbp

The photosensitizer (Compound 3) was prepared according to the procedure described in Example 2, except using 2,9-dimethyl-2,2'-bipyridine ("mbp") as the secondary ligand. The structure of mbp is shown below:

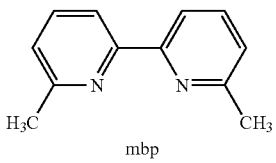

mbp

The structure of the synthesized photosensitizer (Compound 3) is shown below.

Compound 3

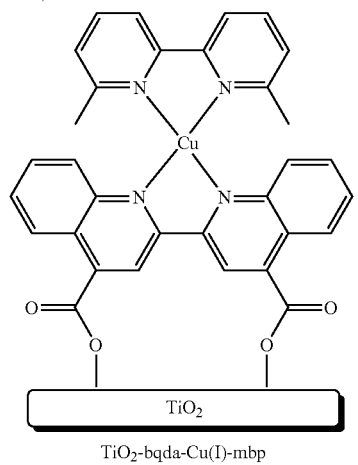

TiO$_2$-bqda-Cu(I)-mbp

The characteristic long wavelength MLCT absorption of the heteroleptic copper complex bqda-Cu(I)-mbp appeared at 527 nm.

EXAMPLE 5

TiO$_2$-bqda-Cu(I)-bap

The photosensitizer (Compound 4) was prepared according to the procedure described in Example 2, except using 4,7-diphenyl-1,10-phenanthroline ("bap") as the secondary ligand. The structure of bap is shown below:

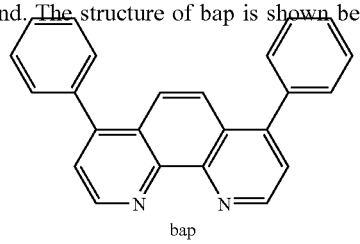

bap

The structure of the synthesized photosensitizer (Compound 4) is shown below.

Compound 4

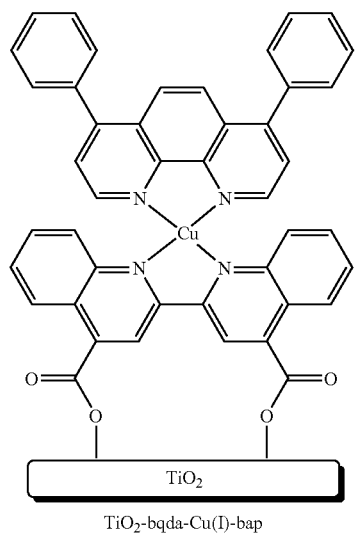

TiO$_2$-bqda-Cu(I)-bap

The characteristic long wavelength MLCT absorption of the heteroleptic copper complex bqda-Cu(I)-bap appeared at 540 nm.

EXAMPLE 6

TiO$_2$-bqda-Cu(I)-phen

The photosensitizer (Compound 5) was prepared according to the procedure described in Example 2, except using 1,10-phenanthroline ("phen") as the secondary ligand. The structure of phen is shown below:

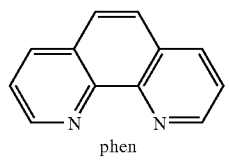

phen

The structure of the synthesized photosensitizer (Compound 5) is shown below.

Compound 5

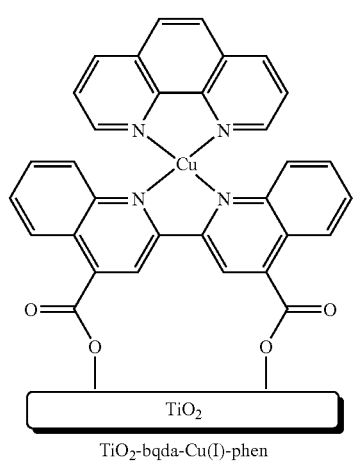

TiO$_2$-bqda-Cu(I)-phen

The characteristic long wavelength MLCT absorption of the heteroleptic copper complex bqda-Cu(I)-phen appeared at 530 nm.

EXAMPLE 7

TiO$_2$-dcpby-Ru(II)-(bpyme)Cl$_2$

A glass plate coated with a TiO$_2$ film was dipped into a saturated solution of 4,4'-dicarboxy-2,2'-bipyridine ("dcbpy") in DMSO/ethanol (v/v 1:20) for a period of 24 hours, washed thoroughly with ethanol, and then air dried at room temperature. The structure for dcbpy is shown below:

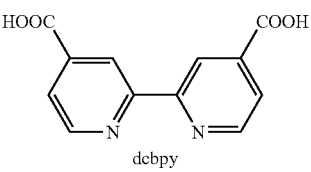

dcbpy

The plate was then dipped into a $10^{-3}$ M DMF solution of Ru(bpyme)(DMSO)$_2$Cl$_2$ and refluxed for 4 hours. The structure of 4,4'-dimethyl-2,2'-bipyridine ("bpyme") is shown below:

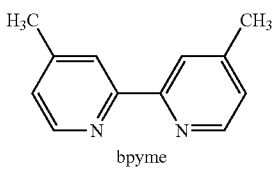

bpyme

The plate was then removed, rinsed with ethanol, and air dried.

The structure of the synthesized photosensitizer (Compound 6) is shown below.

Compound 6

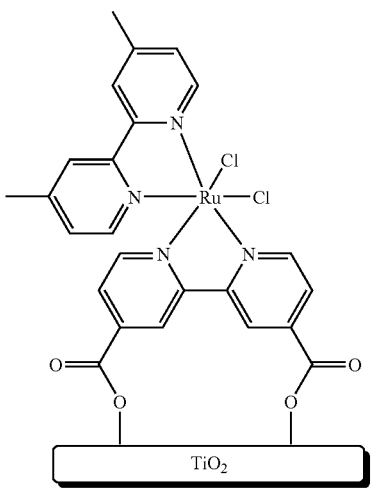

TiO$_2$-dcbpy-Ru(II)-(bpyme)Cl$_2$

EXAMPLE 8

TiO$_2$-tpyda-Fe(II)-(bpyme)Cl

A glass plate coated with a TiO$_2$ film was dipped into $10^{-3}$ M solution of 2,6-di-(2'-quinolinyl-4'-carboxylic acid)pyridine ("tpyda") in DMSO/ethanol (v/v 1:25) for a period of 24 hours, washed thoroughly with ethanol, and then air dried at room temperature. The structure for tpyda is shown below:

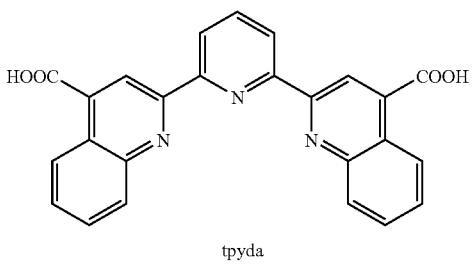

tpyda

The iron(II) complex was then synthesized in a stepwise fashion from the anchored dicarboxylate ligand. First, the plate is dipped into a $10^{-3}$ M ethanol solution of FeCl$_2$ for 3 hours under Ar, rinsed with ethanol, and air dried. The above plate is then dipped into a $10^{-3}$ M dichloromethane solution of a secondary ligand, 4,4'-dimethyl-2,2'-bipyridine ("bpyme") for 18 hours. The structure of the secondary ligand bpyme is shown in Example 7 above. The plate was then washed with dichloromethane and air dried at room temperature.

The structure of the synthesized photosensitizer (Compound 7) is shown below.

Compound 7

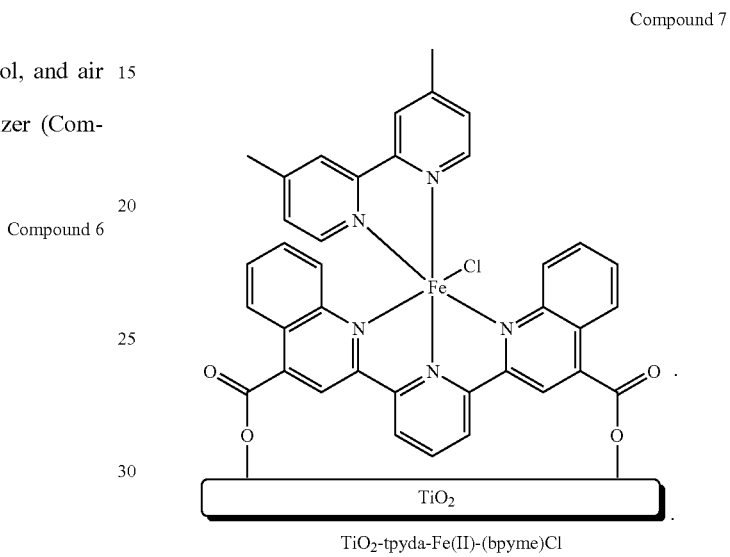

TiO$_2$-tpyda-Fe(II)-(bpyme)Cl

Formation of the complex on the TiO$_2$ film was evidenced by a color change (from light orange to red) of the glass plate. The characteristic long wavelength MLCT absorption appeared at 525 nm.

REFERENCES CITED

The entire content of each of the references below is hereby incorporated by reference:

Alonso-Vante, N.; Jean-Francois, N.; Sauvage, J.-P. "Spectral Sensitization of Large-band-gap semiconductors (Thin Films and Ceramics) by a Carboxylated Bis(1-10-Phenathroline)copper(I) Complex," *J. Chem. Soc., Dalton Trans.* 1994, pp. 1649–1654.

Argazzi, R.; Bignozzi, C. A.; Heimer, T. A.; Castellano, F. N.; Meyer, G. "Enhanced Spectral Sensitivity from Ruthenium(II) Polypyridyl Based Photovoltaic Devices," *J. Inorg. Chem.* 1994, vol. 33, pp. 5741–5759.

Armaroli, N. "Photoactive mono- and polynuclear Cu(I)-phenanthrolines. A viable alternative to Ru(II)-polypyridines?," *Chem. Soc. Rev.* 2001, vol. 30, pp. 113–124.

Beley, M.; Bignozzi, C.-A.; Kirsch, G.; Alebbi, M.; Raboin, J.-C. "New ruthenium bisterpyridinyl complexes, as efficient sensitizers of nanocrystalline, TiO$_2$ films," *Inorganica Chimica Acta* 2000, vol. 318, pp. 197–200.

Bignozzi, C. A.; Argazzi, R.; Kleverlaan, C. J. "Molecular and supramolecular sensitization of nanocrystalline wide band-gap semiconductors with mononuclear and polynuclear metal complexes," *Chem. Soc. Rev.* 2000, vol. 29, pp. 87–96.

Hagfeldt, A.; Grätzel, M. "Molecular Photovoltaics," *Acc. Chem. Res.* 2000, vol. 33, pp. 269–277.

Hara, K.; Sugihara, H.; Singh, L. P.; Islam, A.; Katoh, R.; Yanagida, M.; Sayama, K.; Murata, S.; Arakawa, H. "New Ru(II) phenanthroline complex photosensitizers having different number of carboxyl groups for dye-sensitized solar cells," *Journal of Photochemistry and Photobiology A: Chemistry* 2001, vol. 145, pp. 117–122.

Hara, K.; Sugihara, H.; Tachibana, Y.; Islam, A.; Yanagida, M.; Sayama, K.; Arakawa, H. "Dye-Sensitized Nanocrystalline TiO₂ Solar Cells Based on Ruthenium(II) Phenanthroline Complex Photosensitizers," *Langmuir* 2001, vol. 17, pp. 5992–5999.

Hara, K.; Horiuchi, H.; Katoh, R.; Singh, L. P.; Sugihara, H.; Sayama, K.; Murata, S.; Tachiya, M.; Arakawa, H. "Effect of the Ligand Structure on the Efficiency of Electron Injection from Exited Ru-Phenanthroline Complexes to Nanocrystalline TiO₂ Films," *J. Phys. Chem. B* 2002, vol. 106, pp. 374–379.

Islam, A.; Sugihara, H.; Singh, L. P.; Hara, K.; Katoh, R.; Nagawa, Y.; Yanagida, M.; Takahashi, Y.; Murata, S.; Arakawa, H. "Synthesis and photophysical properties of ruthenium(II) charge transfer sensitizers containing 4,4'-dicarboxy-2,2'-biquinoline and 5,8-dicarboxy-6,7-dihydro-dibenzo[1,10]-phenanthroline," *Inorganica Chimica Acta* 2001, vol. 322, pp. 7–16.

Kalyanasundaram, K.; Grätzel, M. "Applications of functionalized transition metal complexes in photonic and optoelectronic devices," *Coordination Chemistry Reviews* 1998, vol. 77, pp. 347–414.

Kelly, C. A.; Meyer, G. J. "Excited state processes at sensitized nanocrystalline thin film semiconductor interfaces," *Coordination Chemistry Reviews* 2001, vol. 211, pp. 295–315.

Nazeeruddin, M. K.; Kay, A.; Rodicio, I.; Humphry-Baker, R.; Müller, E.; Liska, P.; Vlachopoulos, N.; Grätzel, M. "Conversion of Light to Electricity by cis-X₂Bis(2,2'-bipyridyl-4,4'-dicarboxylate)ruthenium(II) Charge-Transfer Sensitizers (X=Cl⁻, Br⁻, I⁻, CN⁻, and SCN) on Nanocrystalline TiO₂ Electrodes," *J. Am. Chem. Soc.* 1993, vol. 115, pp. 6382–90.

Nazeeruddin, M. K.; Péchy, P.; Renouard, T.; Zakeeruddin, S. M.; Humphry-Baker, R.; Comte, P.; Liska, P.; Cevey, L.; Costa, E.; Shklover, V.; Leone, S.; Deacon, G. B.; Bignozzi, C. A.; Grätzel, M. "Engineering of Efficient Panchromatic Sensitizers for Nanocrystalline TiO₂-Based Solar Cells," *J. Am. Chem. Soc.* 2001, vol. 123, pp. 1613–1624.

Sakaki, S.; Kuroki, T.; Hamada, T. "Synthesis of a new copper(I) complex, [Cu(tmdcbpy=4,4',6,6'-tetramethyl-2,2'-bipyridine-5,5'-dicarboxylic acid), and its application to solar cells," *J. Chem. Soc., Dalton Trans.* 2002, pp. 840–842.

Schwarz, O.; van Loyen, D.; Jockusch, S.; Turro, N. J.; Dürr, H. "Preparation and application of new ruthenium(II) polypyridyl complexes as sensitizers for nanocrystalline TiO₂," *Journal of Photochemistry and Photobiology A: Chemistry* 2000, vol. 132, pp. 91–98.

Yanagida, M.; Islam, A.; Tachibana, Y.; Fujihashi, G.; Katoh, R.; Sugihara, H.; Arakawa, H. "Dye-sensitized solar cells based on nanocrystalline TiO₂ sensitized with a novel pyridylquinoline ruthenium(II) complex," *New J. Chem.* 2002, vol. 26, pp. 963–965.

Zakeeruddin, S. M.; Nazeeruddin, M. K.; Humphry-Baker, R.; Grätzel, M. "Stepwise Assembly of Tris-Heteroleptic Polypyridyl Complexes of Ruthenium(II)," *Inorg. Chem.* 1998, vol. 37, pp. 5251–5259.

What is claimed is:

1. A method for in situ, stepwise, solid state synthesis of photosensitizers for titanium dioxide, comprising:

providing an anchor ligand having an anchoring end and a chelating end, wherein the anchor ligand is 4,4'-dicarboxy-2,2'-biquinoline ("bqda");

binding the anchoring end of the anchor ligand onto the titanium dioxide to give a bound anchor ligand with the chelating end;

incorporating a metal cation onto the chelating end of the bound anchor ligand to give a bound metal, wherein the metal cation is copper ("Cu"); and binding one or more secondary ligands onto the bound metal, wherein the one or more secondary ligands are 2,2'-biquinoline ("biq"), 2,9-dimethyl-1,10-phenanthroline ("mph"), 2,9-dimethyl-2,2'-bipyridine ("mbp"), 4,7-diphenyl-1,10-phenanthroline ("bap"), or 1,10-phenanthroline ("phen").

2. The method of claim 1, wherein the metal cation is a transition metal cation.

3. The method of claim 1, wherein the metal cation further possesses additional inorganic ligands, organic ligands, counterions, or a combination thereof.

4. The method of claim 1, wherein the one or more secondary ligands independently are the same or different.

5. The photosensitizer for titanium dioxide prepared according to the method of claim 1.

6. A photosensitizer having a general structure:

TiO2-Anchor Ligand-M-Secondary Ligand, wherein the Anchor Ligand is 4,4'-dicarboxy-2,2'-biquinoline ("bqda"), wherein M is a metal cation, and wherein the metal cation is copper ("Cu"), and wherein the Secondary Ligand is 2,2'-biquinoline ("biq") 2,9-dimethyl-1,10-phenanthroline ("mph"), 2,9-dimethyl-2,2'-bipyridine ("mbp"), 4,7-diphenyl-1,10-phenanthroline ("bap"), or 1,10-phenanthroline ("phen").

7. The photosensitizer of claim 6, wherein M is a transition metal cation.

8. The photosensitizer of claim 6, wherein M possesses additional inorganic ligands, organic ligands, counterions, or a combination thereof.

9. The photosensitizer of claim 6, wherein the secondary ligand is one or more secondary ligands.

10. The photosensitizer of claim 9, wherein the one or more secondary ligands independently are the same or different.

11. The photosensitizer of claim 6, wherein the general structure is:

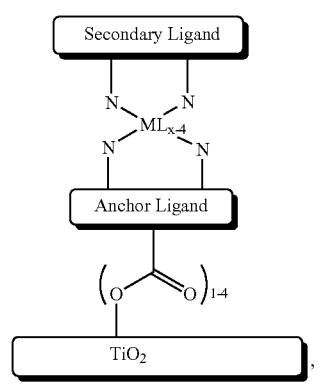

wherein L comprises an inorganic ligand, organic ligand, counterion, or a combination thereof; and wherein x comprises an integer in a range of from four to six.

12. The photosensitizer of claim 11, wherein the structure is:

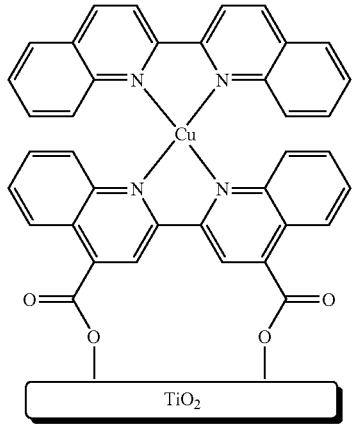

13. The photosensitizer of claim 11, wherein the structure is:

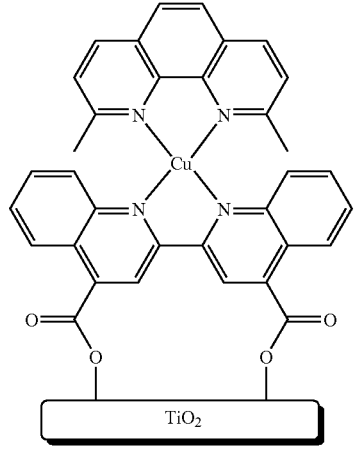

14. The photosensitizer of claim 11, wherein the structure is:

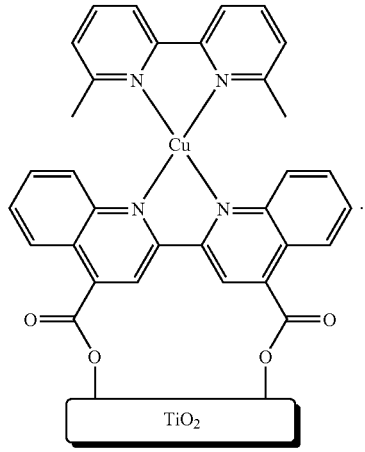

15. The photosensitizer of claim 11, wherein the structure is:

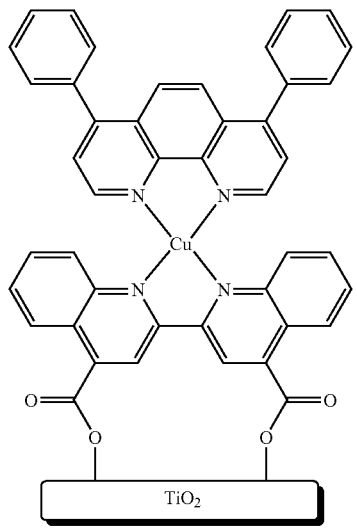

16. The photosensitizer of claim 11, wherein the structure is:

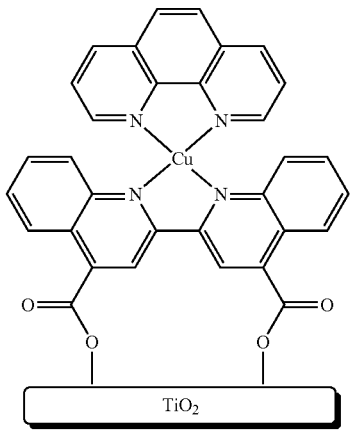

* * * * *